(12) United States Patent
Andersson

(10) Patent No.: US 12,203,712 B2
(45) Date of Patent: Jan. 21, 2025

(54) PREVENTION OF MICROBIOLOGICAL GROWTH IN HEAT EXCHANGERS

(71) Applicant: ALFA LAVAL CORPORATE AB, Lund (SE)

(72) Inventor: Thomas Andersson, Kungsor (SE)

(73) Assignee: ALFA LAVAL CORPORATE AB, Lund (SE)

( * ) Notice: Subject to any disclaimer, the term of this patent is extended or adjusted under 35 U.S.C. 154(b) by 0 days.

(21) Appl. No.: 17/766,579

(22) PCT Filed: Oct. 6, 2020

(86) PCT No.: PCT/EP2020/077902
§ 371 (c)(1),
(2) Date: Apr. 5, 2022

(87) PCT Pub. No.: WO2021/069395
PCT Pub. Date: Apr. 15, 2021

(65) Prior Publication Data
US 2023/0417497 A1    Dec. 28, 2023

(30) Foreign Application Priority Data

Oct. 7, 2019  (EP) ..................................... 19201662
May 26, 2020  (SE) ..................................... 2050606-9

(51) Int. Cl.
*F28F 19/00*    (2006.01)
*A23L 3/22*    (2006.01)
(Continued)

(52) U.S. Cl.
CPC .............. *F28F 19/004* (2013.01); *A23L 3/22* (2013.01); *A61L 2/03* (2013.01); *F28D 7/16* (2013.01); *F28F 13/16* (2013.01); *F28F 2265/20* (2013.01)

(58) Field of Classification Search
CPC . F28F 19/004; F28F 13/16; A23L 3/22; F28D 7/16
See application file for complete search history.

(56) References Cited

U.S. PATENT DOCUMENTS 3,798,142 A * 3/1974 Evans ..................... C23F 13/02
                                                                   165/186
4,056,142 A * 11/1977 Baumann .............. F28F 19/004
                                                                   204/196.06

(Continued)

FOREIGN PATENT DOCUMENTS

EP    2 372 292 A2    10/2011
EP    3 315 841 A1    5/2018
(Continued)

OTHER PUBLICATIONS

International Search Report on corresponding PCT application (PCT/EP2020/077902) from International Searching Authority (EPO) dated Nov. 19, 2020.

(Continued)

*Primary Examiner* — Jon T. Schermerhorn, Jr.
(74) *Attorney, Agent, or Firm* — Birch, Stewart, Kolasch & Birch, LLP

(57) ABSTRACT

A heat exchanger assembly (10) is proposed comprising: a heat exchanger (12) forming one or more electrically connected partitions (26) separating a first fluid (22) and a second fluid (24). The assembly (10) further comprises: a first electrical connector (14) and a second electrical connector (16) that are operationally connected to the partitions (26) of the heat exchanger (12) and an electrical power source (18) operationally connected to the first electrical connector (14) and the second electrical connector (16). The electrical power source (18) is configured to supply an electric current to the one or more partitions (26) of the heat (Continued)

exchanger (12) via the first electrical connector (14) and the second electrical connector (16).

10 Claims, 3 Drawing Sheets

(51) Int. Cl.
*A61L 2/03* (2006.01)
*F28D 7/16* (2006.01)
*F28F 13/16* (2006.01)

(56) References Cited

U.S. PATENT DOCUMENTS

| | | | | |
|---|---|---|---|---|
| 4,586,562 | A * | 5/1986 | Carlson | F28F 19/004 204/196.05 |
| 4,800,007 | A * | 1/1989 | Karlsson | F28F 19/004 165/186 |
| 5,513,694 | A * | 5/1996 | Cameron | F28F 19/004 204/196.05 |
| 7,225,863 | B2 * | 6/2007 | Anastasijevic | C23F 13/005 165/134.1 |
| 11,454,345 | B2 * | 9/2022 | Andersson | A61L 2/03 |
| 2002/0108849 | A1 | 8/2002 | Inagaki et al. | |
| 2005/0006905 | A1 | 1/2005 | Rurup | |
| 2007/0017811 | A1 * | 1/2007 | Waskaas | B08B 17/00 204/196.01 |
| 2007/0039717 | A1 * | 2/2007 | Inagaki | H01L 23/473 165/172 |
| 2011/0041515 | A1 * | 2/2011 | Fraim | F28F 19/004 165/104.27 |
| 2013/0034644 | A1 | 2/2013 | De-Principe et al. | |
| 2013/0233508 | A1 | 9/2013 | Cederberg et al. | |
| 2016/0106139 | A1 | 4/2016 | Tacke et al. | |
| 2016/0265856 | A1 * | 9/2016 | Saveliev | F28F 13/16 |

FOREIGN PATENT DOCUMENTS

| | | | |
|---|---|---|---|
| EP | 3315841 | 5/2018 | |
| EP | 3332653 | 6/2018 | |
| EP | 3315841 B1 * | 3/2019 | A61L 2/03 |
| GB | 1522716 | 8/1978 | |
| JP | 2005-147479 A | 6/2005 | |
| JP | 2005-337643 A | 12/2005 | |
| JP | 2016-202002 A | 12/2016 | |
| KR | 10-1789541 B1 | 10/2017 | |

OTHER PUBLICATIONS

Written Opinion on corresponding PCT application (PCT/EP2020/077902) from International Searching Authority (EPO) dated Nov. 19, 2020.

Japanese Office Action for Japanese Application No. 2022-546723, dated Nov. 5, 2024, with an English translation.

* cited by examiner

PREVENTION OF MICROBIOLOGICAL GROWTH IN HEAT EXCHANGERS

CROSS-REFERENCE TO RELATED APPLICATION

This application is the National Phase, under 35 U.S.C. § 371(c), of International Application No. PCT/EP2020/077902, filed Oct. 6, 2020, which claims priority from European Application No. EP 19201662.4, filed Oct. 7, 2019, and Swedish Application No. SE 2050606-9, filed May 26, 2020.

FEDERALLY SPONSORED RESEARCH OR DEVELOPMENT

Not Applicable.

TECHNICAL FIELD

The proposed technology relates generally to the field of heat exchangers. It relates specifically to plate heat exchangers and heat exchangers in marine applications. The technology also relates to the prevention of the growth of microorganisms on the inside surfaces of heat exchangers.

BACKGROUND

Heat exchangers are systems that are used to transfer heat between two or more fluids. Typically, the fluids are separated by a solid partition to prevent mixing. Heat exchangers are used in both cooling and heating processes.

Microbiological growth in heat exchangers is a recognized problem. Such growth can negatively affect the performance of the heat exchanger, for example with respect to flow rates and heat conductance. Microbiological growth is particularly a problem in marine applications, in which sea water is supplied to the heat exchangers. Sea water can be high in nutrients and the temperature of the supplied sea water is often within a range that is favorable for microbiological growth.

Liquid food products, such as beverages and liquid dairy products, also have a high nutrient content. Heat exchangers used in the processing of such products typically have high rates of microbiological growth and require a frequent cleaning to prevent a drop in quality of the product. Typically, the production must be interrupted for cleaning and chemicals are commonly used in the cleaning, which contributes to a decreased efficiency and increased production costs.

The microbiological growth is particularly a problem in plate heat exchanger that cannot be disassembled for manual cleaning.

OBJECT

The proposed technology aims at preventing or reducing microbiological growth in heat exchangers, and in particular on the partitions of heat exchangers. It is also an object to reduce microbial growth in heat exchanger used in the processing of liquid food products, and specifically in plate heat exchangers.

SUMMARY

In a first aspect of the proposed technology, a heat exchanger assembly is provided. The assembly comprises: a heat exchanger forming, or comprising, one or more partitions, or walls, separating, or configured to separate or keep distinct, a first fluid and a second fluid and through which heat can be transferred, or conducted, between the first fluid and the second fluid. The assembly further comprises: a first electrical connector and a second electrical connector that are operationally connected to the one or more partitions, or walls, of the heat exchanger. Additionally, the assembly comprises an electrical power source operationally connected to the first electrical connector and the second electrical connector and configured to supply an electric current, and/or an electric potential, to the one or more partitions, or walls, of the heat exchanger via the first electrical connector and the second electrical connector.

A partition is here and throughout these specifications understood to encompass a wall. It is understood that the first aspect of the proposed technology is directed to a heat exchanger assembly for reducing, inhibiting, or preventing growth of microorganisms in the heat exchanger forming part of the assembly. Operationally connected is here understood to only specify that there is an electrical connection by which a current can be supplied.

The first and second electrical connectors being operationally connected to the one or more partitions encompasses the connectors being operationally connected to each of the one or more partitions. It is also understood to encompass the electrical connectors being directly connected to the partitions, and the electrical connectors being directly connected to one of the partitions, which in turn is electrically connected to the other partitions, for example by way of being pressed together, by welding, or by brazing.

The first fluid and the second fluid may be liquids. The assembly allows for the prevention of growth of microorganisms on the one or more partitions. The electrical power source may be configured to supply an electric current or electric potential for reducing, inhibiting, or preventing growth of microorganisms in the heat exchanger, or on the one or more partitions of the heat exchanger. In extension, the assembly allows for a reduction of the generation or growth of a biofilm on the one or more partitions. Microorganisms are here understood to encompass unicellular organisms that may exist in single-celled forms or in colonies of cells, and microscopic multicellular organisms.

The growth conditions may depend on microbial nutrients, temperature, and oxygen level in the fluids. For example, sea water at about 40 degrees C. provides better growth condition than chlorinated tap water at about 10 degrees C.

It is understood that the one or more partitions are electrically conductive. They may be formed of a metal or a combination of metals, e.g. an alloy. It is also understood that one of the electrical connectors, such as the second electrical connector, may be grounded or earthed, for example by way of the hull of a ship. If an alternating electric current is supplied by the electrical power source, this means that the neutral and earth are shared and that the phase is provided by the other electrical connector.

It is understood that the heat exchanger may be a shell and tube heat exchanger, plate heat exchanger, plate and shell heat exchanger, plate fin heat exchanger, or a pillow plate heat exchanger.

The first electrical connector and the second electrical connector may be spaced apart at, or on, the heat exchanger. The one or more partitions may extend from a first end of the heat exchanger to an opposite second end of the heat exchanger, and the first electric connector and the second electrical connector may connect to the one or more partitions at the first end and the second end, respectively, of the heat exchanger.

For example, the heat exchanger may be a shell and tube heat exchanger comprising a tube bundle with straight tubes forming the one or more partitions and a shell enclosing the tube bundle. The first electrical connector and the second electrical connector may be connected to each of the tubes at opposite ends of the tube bundle.

The one or more partitions may further contain or enclose the first fluid and the second fluid inside the heat exchanger. This means that both the first fluid and the second fluid are surrounded by the one or more partitions when they pass through the heat exchanger, and that the flow of the first fluid and the second fluid is restricted, or contained, by the one or more partitions when passing through the heat exchanger. The one or more partitions may form a plurality of partitions.

The heat exchanger may further comprise a shell configured to contain the first fluid and/or the second fluid. For example, the shell may be the two outermost plates in a plate heat exchanger, or the shell of a shell and tube heat exchanger.

The one or more, or plurality of, partitions may form one or more, or a plurality of, first channels through which the first fluid can flow. For example, the heat exchanger may be a shell and tube heat exchanger comprising a tube bundle with tubes constituting the partitions forming a plurality of first channels.

Similarly, the one or more, or plurality of, partitions may form one or more, or a plurality of, second channels through which the second fluid can flow. For example, the heat exchanger may be a plate heat exchanger comprising a plurality of plates forming the one or more partitions, the one or more first channels, and the one or more second channels.

In a second aspect of the proposed technology, a method is provided for reducing, inhibiting, or preventing microbiological growth in a heat exchanger of a heat exchanger assembly according to the first aspect of the proposed technology. The method comprises: supplying an electric current, and/or an electric potential, to the one or more partitions of the heat exchanger with the electrical power source. The method may further comprise: providing a flow of the first fluid and a flow of the second fluid in, or through, the heat exchanger. The electric current, and/or an electric potential, may be configured for reducing, inhibiting, or preventing growth of microorganisms in the heat exchanger, or on the one or more partitions of the heat exchanger.

In a third aspect of the proposed technology, a system is provided for preventing microbiological growth in a heat exchanger forming one or more partitions separating a first fluid and a second fluid and through which heat can be transferred between the first fluid and the second fluid. The system comprises: a first electrical connector and a second electrical connector adapted for operationally connecting to the one or more partitions of the heat exchanger. Additionally, the assembly comprises: an electrical power source adapted for operationally connecting to the first electrical connector and the second electrical connector and configured to supply an electric current, and/or an electric potential, to the one or more partitions of the heat exchanger via the first electrical connector and the second electrical connector.

As for the first aspect of the proposed technology, the electrical power source may be configured to supply an electric current or electric potential for reducing, inhibiting, or preventing growth of microorganisms in the heat exchanger, or on the one or more partitions of the heat exchanger.

In a fourth aspect of the proposed technology, a method is provided for reducing, inhibiting, or preventing microbiological growth in a heat exchanger forming one or more partitions separating a first fluid and a second fluid and through which heat can be transferred between the first fluid and the second fluid. The method comprises: providing a system according to the third aspect of the proposed technology, operationally connecting the first electrical connector and the second electrical connector to the one or more partitions of the heat exchanger, and supplying an electric current, and/or an electric potential, to the one or more partitions of the heat exchanger with the electrical power source. The method may further comprise: providing a flow of the first fluid and a flow of the second fluid in the heat exchanger. The electric current, and/or an electric potential, may be configured for reducing, inhibiting, or preventing growth of microorganisms in the heat exchanger, or on the one or more partitions of the heat exchanger.

In a fifth aspect of the proposed technology, a pasteurizer is provided for heat treatment of a liquid food product, or of a liquid constituent of a food product, wherein the pasteurizer comprises a heat exchanger assembly according to the first aspect of the proposed technology for heating or cooling the liquid food product. The first fluid may be the liquid food product. The second fluid may be a heating fluid, such as hot water or steam, or a cooling liquid, such as cold water, a brine solution, or an alcohol solution, such as glycol. A liquid constituent of a food product is here to be regarded as a liquid food product.

It the abovementioned heat exchanger assembly is for heating, the pasteurizer may further comprise an additional heat exchanger assembly according to the first aspect of the proposed technology for cooling the liquid food product. The first fluid may be the liquid food product. The second fluid may be a cooling liquid, such as cold water, a brine solution, or an alcohol solution, such as glycol. Alternatively, the two heat exchanger assemblies may be operationally connected to provide a regenerative heating and cooling.

Further optional features of the proposed technology are described below.

The heat exchanger may have more than one partition, or a plurality of partitions. Neighboring partitions, or all of the partitions, may be electrically connected or coupled to one another, or the partitions may be configured to be on, or share, the same electric potential, or the heat exchanger is configured with the partitions on, or sharing, the same electric potential. This means that the partitions are not electrically insulated from one another, for example by non-conductive spacers separating the partitions. This also means that the voltage difference between partitions is small or insignificant. The partitions being electrically connected may be achieved by the partitions contacting each other, for example by pressing the partitions together. It may also be achieved by the partitions being joined, for example by soldering, welding, or brazing, or by the partitions being connected by an electrically conductive connector or support. This means that all partitions more or less are on the same electric potential. It also means that the electric potential within the heat exchanger is minimized and that no significant electric poles are generated that can induce chemical reactions with negative impact on the first fluid and/or the second fluid. For example, if the first fluid and the second fluid may contain water, an electric potential within the heat exchanger can produce hydrogen and oxygen by electrolysis in the fluids.

Apart from the first electrical connector and a second electrical connector operationally connecting to the one or more partitions of the heat exchanger, the heat exchanger may be electrically insulated from the surroundings. To achieve this, the heat exchanger assembly may comprise an electrically insulating support supporting the heat exchanger. For example, the electrically insulating support may be formed of an electrically non-conductive thermoplastic material. This contributes to electrically insulating the partitions of the heat exchanger from the surroundings, which in extension contributes to an improved prevention of microbiological growth.

Additionally, the heat exchanger assembly may comprise a plurality of conduits that are connected to the heat exchanger and configured to supply the first fluid and the second fluid to the heat exchanger. The plurality of conduits may further be configured to drain the first fluid and the second fluid from the heat exchanger. The plurality of conduits may be electrically insulating. For example, the conduits may be formed of an electrically non-conductive thermoplastic material. This contributes to electrically insulating the partitions of the heat exchanger from the surroundings.

The heat exchanger assembly may further comprise a plurality of joints operationally connecting the plurality of conduits to the heat exchanger, wherein the joints are electrically insulating. For example, the joints may be formed of an electrically non-conductive thermoplastic material. This contributes to electrically insulating the partitions of the heat exchanger from the surroundings.

The heat exchanger may be configured to handle sea water. The first fluid may be sea water. This means that the first fluid contains salts and typically also significant amounts of nutrients for microorganisms. Additionally, or alternatively, the heat exchanger may be configured to handle liquid food products, or liquid constituents of a food product. For example, the first fluid may be a beverage, or liquid constituents of a beverage. The heat exchanger may be configured to handle a beverage or its constituent. The first fluid may be a liquid dairy product, or a liquid constituent of a dairy product. For example, the first fluid may be colostrum from dairy cattle. The heat exchanger may be configured to handle liquid dairy products or constituents.

The heat exchanger may be a plate heat exchanger comprising a plurality of plates, or parallel plates, forming the one or more partitions. For example, the heat exchanger may be composed of 20 plates, of which two are outer plates and 18 are inner plates forming 18 partitions separating the first fluid and the second fluid. It is understood that the plurality of plates are of an electrically conductive material. The plates may be formed by a metal or a combination of metals, e.g. an alloy. For example, the plates may be formed of stainless steel, titanium, or a titanium alloy.

The plurality of plates may be electrically connected or coupled to one another, or the plurality of plates may be configured to be on the same electric potential. For example, this may be achieved by the plates being structurally connected, or physically connected or contacting, for example by being pressed together by metal clamps or screws, or by neighboring plates being joined together by welding or brazing. This means that the plates are not electrically insulated from one another, for example by non-conductive spacers separating the plates. This also means that the plates cannot be on different electrical potential, such as one plate being on a negative potential and a neighboring plate being on a positive potential.

The first electrical connector and the second electrical connector may be structurally connected to different plates of the plurality of plates. This has the effect that the electrical power source can generate an electric potential that on average has a component that is transverse to the plates. It is contemplated that this contributes to an improved performance. Structurally connected to a plate is here understood to encompass the electrical connector being connected directly, or forming physical connection, to the plate. Alternatively, the first electrical connector and the second electrical connector may be structurally connected to the same plates of the plurality of plates.

It is understood that the electrical connectors can be structurally connected to two, or more than two plates, at the same time.

The conditions for microbial growth may be greater, or more favorable, in the first fluid than in the second fluid, and the first electrical connector may be structurally connected to a pair of adjacent, or juxtaposed, plates of the plurality of plates. The pair of adjacent plates may enclose the first fluid or provide a channel for the first fluid. The pair of adjacent plates may be structurally and/or electrically connected, to one another, or configured to be on the same electric potential. Similarly, the second electrical connector may be structurally connected to the pair of adjacent plates. Structurally connected is understood to encompass two elements being physically contacting, for example by being pressed or soldered together. This contributes to an optimized travel of the current through the plate heat exchanger for preventing microbiological growth.

The first electrical connector and the second electrical connector may be structurally connected to the heat exchanger, or to the plurality of plates, on opposite sides of the heat exchanger. This has the effect that the electrical power source can generate an electric potential having a component that is parallel to and crosses the plates. Structurally connected to the heat exchanger is here understood to encompass the electrical connector being connected directly, or forming physical connection, to the heat exchanger. It is contemplated that this contributes to an optimized travel of the current for preventing microbiological growth.

The plates of the heat exchanger may have the same outer shape, or similar outer shapes, and the plates may be oriented in the same direction, or to form a stack of plates.

A plate, or each plate, of the plurality of parallel plates may have four side sections and four corner sections, each corner section being located between two side sections, wherein the first electrical connector is structurally connected to a first corner section, and the second electrical connector is structurally connected to a second corner section, wherein the second corner section is diagonal to the first corner section. The second corner section being diagonal to the first corner section means that said corner sections are connected by a side section, a corner section, and an additional side section on either side of the first corner section.

In a different wording, a plate, or each plate, of the plurality of parallel plates may have a generally rectangular shape with four corners, and the first electrical connector and the second electrical connector may be structurally connected at different corners that are located diagonally with respect to one another, or with respect to the plates.

The heat exchanger may be a shell and tube heat exchanger comprising a tube bundle forming the one or more partitions and a shell enclosing the tube bundle. The heat exchanger may be a straight-tube heat exchanger. The first electrical connector may be connected to each of the tubes by way of a first tube support supporting the tube bundle, for example at a first end of the tube bundle. Additionally, the second electrical connector may be connected to each of the tubes by way of a second tube support supporting the tube bundle, for example at a second end of the tube bundle. Each of the tubes of the tube bundle may have an inlet at the first tube support and an outlet at the second tube support. The first tube support may be a first tube sheet or a first tube plate connecting to the shell and separating the first fluid and the second fluid. Similarly, the second tube support may be a second tube sheet or a second tube plate connecting to the shell and separating the first fluid and the second fluid.

The first tube support and the shell may form a first enclosed space configured to contain the first fluid. The heat exchanger may further comprise an inlet, for example formed by the shell, arranged to allow the first fluid to enter first enclosed space from outside the shell. Similarly, the second tube support and the shell may form a second enclosed space configured to contain the first fluid. The heat exchanger may further comprise an outlet, for example formed by the shell, arranged to allow the first fluid to exit the first enclosed space to the outside the shell. The first tube support and the second tube support may be electrically insulated from the shell.

The first tube support, the second tube support, and the shell may form a third enclosed space configured to contain the second fluid and through which the tubes extend, wherein the heat exchanger further comprises inlets and outlets arranged to allow the second fluid to enter and leave the third enclosed space, respectively, and to allow the second fluid to pass outside the tubes in the third enclosed space. The tubes may extend from the first enclosed space to the second enclosed space via the third enclosed space and allow a flow of the first fluid from the first enclosed space to the second enclosed space without mixing with the second fluid.

The inlets and outlets for the second fluid may be formed by the shell. The third enclosed space may have cylindrical outer shape, which may have a circular or rectangular cross-section.

Alternatively, the heat exchanger may be a U-tube heat exchanger. The first electrical connector may be connected to each of the tubes by way of a first tube support supporting the tube bundle, for example at a first end of the tube bundle. Additionally, the second electrical connector may be connected to each of the tubes at a second end of the tube bundle. Each of the tubes of the tube bundle may have an inlet and an outlet at the first tube support. The first tube support may be a first tube sheet or a first tube plate connecting to the shell and separating the first fluid and the second fluid.

The first tube support and the shell may form a first enclosed space configured to contain the first fluid. The heat exchanger may further comprise an inlet, for example formed by the shell, arranged to allow the first fluid to enter first enclosed space from outside the shell. Similarly, the first tube support and the shell may form a second enclosed space configured to contain the first fluid. The heat exchanger may further comprise an outlet, for example formed by the shell, arranged to allow the first fluid to exit the first enclosed space to outside the shell. The first tube support may be electrically insulated from the shell.

The first tube support and the shell may form a third enclosed space configured to contain the second fluid and through which the tubes extend, wherein the heat exchanger further comprises inlets and outlets arranged to allow the second fluid to enter and leave the third enclosed space, respectively, and to allow the second fluid to pass the outer surfaces of the tubes in the third enclosed space. The inlets and outlets for the second fluid may be formed by the shell. The electric current may be an alternating current. The alternating current may have a square wave form. This means that the peak voltage is approximately equal to the root-mean square voltage. It has been found that this type of current inhibits microbiological growth.

The alternating current may be below 10 mA, below 1 mA, between 0.1 mA and 1 mA, or between 0.3 mA and 0.7 mA. It has been found that this current is sufficient for inhibiting microbiological growth. The alternating current may have a frequency below 100 Hz, below 10 Hz, or below 1 Hz. The alternating current may be supplied at a peak voltage below 120 V, in the range 40 V to 100 V, or in the range 70 to 90 V. Additionally or alternatively, the alternating current may have a duty cycle of about 50%.

The first fluid and/or the second fluid may contain or comprise water and the heat exchanger assembly may be configured for avoiding or preventing electrolysis of the water, or the heat exchanger assembly may be configured to avoid or prevent the heat exchanger from functioning as an electrolytic cell during operation. For example, this can be achieved by having neighboring, or all, partitions and any surrounding shell on the same electric potential.

BRIEF DESCRIPTION OF THE DRAWINGS

A more complete understanding of the abovementioned and other features and advantages of the proposed technology will be apparent from the following detailed description of preferred embodiments in conjunction with the appended drawings, wherein.

DESCRIPTION OF THE DRAWINGS

Figure 1:
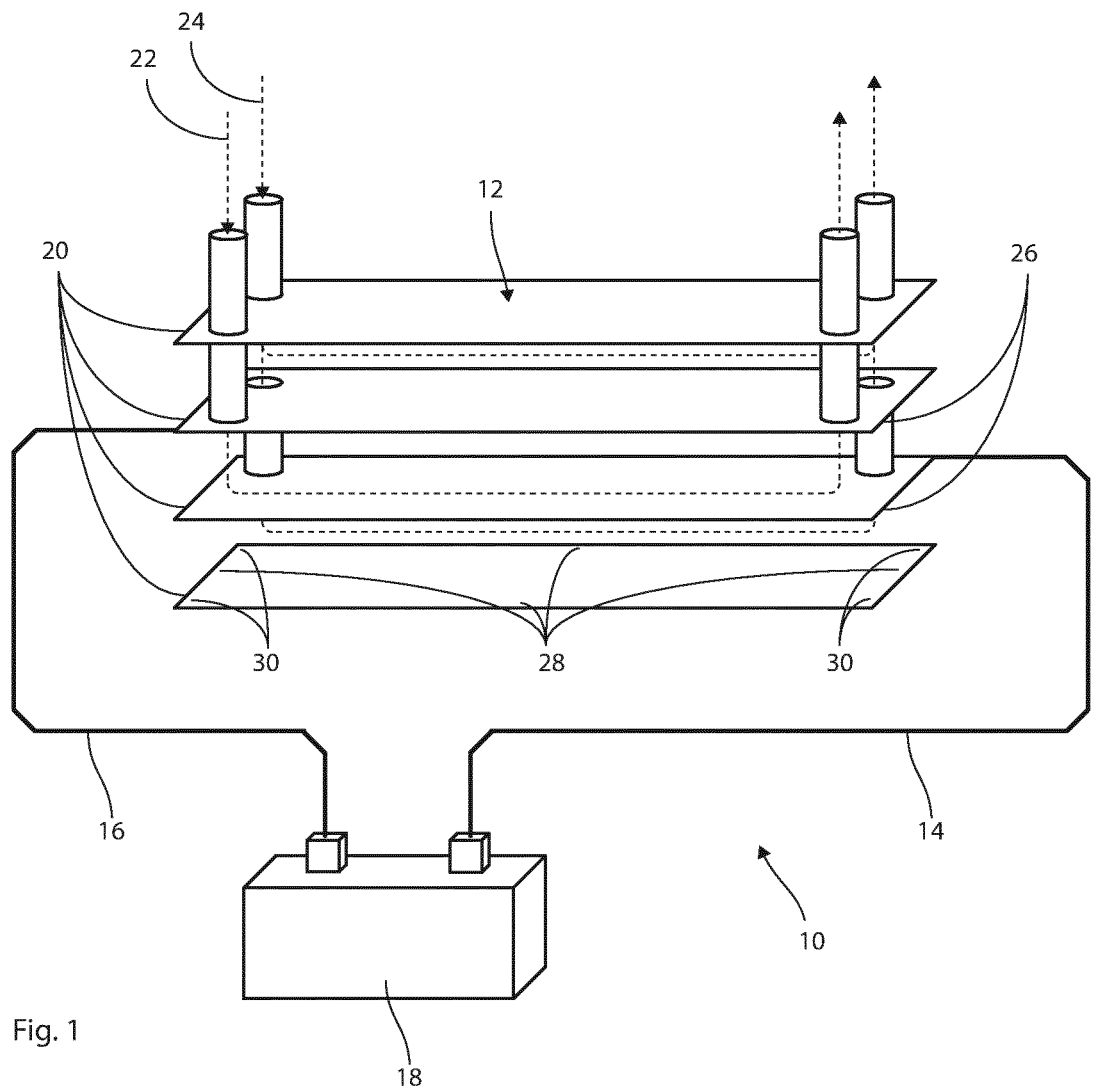
FIG. 1 is a schematic view of an embodiment of a heat exchanger assembly with a plate heat exchanger.

An embodiment of a heat exchanger assembly 10 is schematically illustrated in FIG. 1. It is composed of a heat exchanger 12, a first electrical connector 14, a second electrical connector 16, and an electrical power source 18. The heat exchanger 14 is a plate heat exchanger having four parallel plates 20. The plates are rectangular and of stainless steel. This means that each plate 20 has four side sections 28 and four corner sections 3 as indicated in FIG. 1.

The plates 20 are joined at the edges (not shown) and forms three channels in which a first fluid 22 and a second fluid 24 flow as indicated by the dashed lines in FIG. 1. The first fluid 22 is sea water and the second fluid 24 is fresh water. The flows of the first fluid 22 and the second fluid 24 are generated or provided by pumps (not shown). The flow directions of the first fluid 22 and the second fluid 24 are indicated by arrows in FIG. 1, which shows concurrent flows. In alternative embodiments the flows can be countercurrent, which is achieved by reversing the flow of either the first fluid 22 or the second fluid 24.

The two central plates 20 form two partitions 26 between which the first fluid 22 flows, thus separating the first fluid 22 from the second fluid 24. Heat can be transferred between the first fluid 22 and the second fluid 24 through the two partitions 26. In this embodiment, the first fluid 22 has a higher temperature than the second fluid 24 and heat is transferred from the former to the latter.

The first electrical connector 14 and the second electrical connector 16 are electrical wires that are attached to the inner plates 20 by clamps (not shown). The first electrical connector 14 is connected to the lower inner plates 20 and the second electrical connector is connected to the other upper inner plate 20, as is shown in FIG. 1. This means that the first electrical connector 14 and a second electrical connector 16 are structurally connected to different inner plates 20, and also operationally connected to the separating partitions 26. They are also attached at diagonally opposite corner sections 30 of the inner plates 20, as is shown in FIG. 1. This means that the first electrical connector 14 and the second electrical connector 16 are spaced apart at the heat exchanger 12, that they are structurally connected to the heat exchanger 12 on opposite sides of the heat exchanger 12, and that they are structurally connected at different corners that are located diagonally with respect to one another.

In an alternative embodiment, the first electrical connector 14 is connected to both inner plates 20 and the second connector 16 is also connected only to both inner plates 20.

The first electrical connector 14 and the second electrical connector 16 are connected to the output terminals of the electrical power source 18. This way the electrical power source 18 can supply an electric current and an electric potential to the separating partitions 26 via the first electrical connector 14 and the second electrical connector 16. In an alternative embodiment, the second electrical connector 16 is electrically grounded to earth.

There are rubber gaskets (not shown) between the plates 20 preventing leakage of the first fluid 22 and the second fluid 24 from the heat exchanger 12. The plates 20 are pressed together and held in place by metal screw clamps (not shown) contacting all plates 20. This means that the plates are electrically connected, and in extension that the separating partitions 26 are electrically connected to one another.

The electrical power source 18 supplies an alternating electric current in the form of a square wave to the first electrical connector 14 and the second electrical connector 16, and in extension to the one or more separating partitions 26. The alternating current has an electric peak current between 0.3 mA and 0.7 mA, a frequency below 1 Hz, and a duty cycle of about 50%. The alternating current is supplied at a peak voltage in the range 70 to 90 V.

Figure 2:
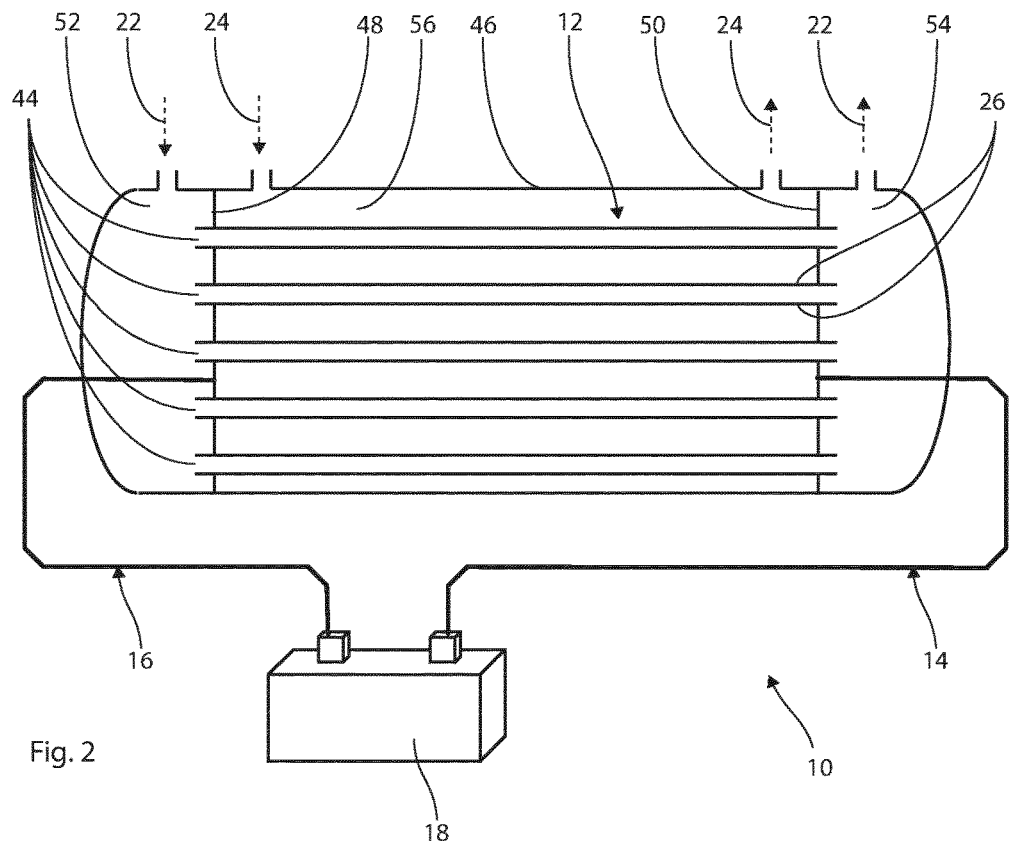
FIG. 2 is a schematic view of an embodiment of a heat exchanger assembly with a straight-tube heat exchanger.

Another embodiment of a heat exchanger assembly 10 is schematically illustrated in FIG. 2. Components having the same nature or function, or with similar nature or function, as in the embodiment described in relation to FIG. 1 have been given the same reference number. The heat exchanger 12 is a shell and tube heat exchanger. It has a tube bundle of straight tubes 44 forming the one or more partitions 26 and a shell 46 that encloses the tube bundle.

Each of the straight tubes 44 are supported at one end by a first tube plate 48 constituting a first tube support and at the other end by a second tube plate 50 constituting a second tube support. Each of the straight tubes 44 has an inlet at the first tube plate 48 and an outlet at the second tube plate 50.

The straight tubes 44, the first tube plate 48 and the second tube plate 50 are of metal and are welded together. This way the components in question are electrically connected to one another and are on the same electric potential.

The first electrical connector 14 and the second electrical connector 16 are composed of the first tube plate 48 and the second tube plate 50, respectively, and of electric cables connecting the tube plates 48 and 50 to the electrical power source 18. This way, the electrical power source 18 is configured to supply an electric current to the tubes 44, and in extension to the separating partitions 26.

The first tube plate 48 and the second tube plate 50 connect to the shell 46 and separates the first fluid 22 from the second fluid 24. The tube plates 48 and 50 are electrically insulated from the shell 46 by way of a rubber gasket (not shown).

The first tube plate 48 and the shell 46 forms a first enclosed space 52 that can contain the first fluid 22. The heat exchanger 12 has an inlet in the shell 46 through which the first fluid enters the first enclosed space 52. The second tube plate 50 and the shell 46 form a second enclosed space 54 that can contain the first fluid 22. The heat exchanger 12 has an outlet in the shell 46 through which the first fluid 12 can leave the second enclosed space 54. The inlets of the tubes 44 open to the first enclosed space 52 and the outlets of the tubes 44 open to the second enclosed space 54.

The first tube plate 48, the second tube plate 50, and the shell 46 form a third enclosed space 56 that can contain the second fluid 24. The heat exchanger 12 has an inlet and outlet in the shell 46 through which the second fluid 24 can enter and leave the third enclosed space 56.

Each tube 44 extends from the first enclosed space 52 to the second enclosed space 54 via the third enclosed space 56, thus constituting a first channel through which the first fluid 22 can flow from the first enclosed space 52 to the second enclosed space 54 and pass the second fluid 24 without mixing, thus allowing a heat transfer between the fluids 22 and 24. The inlets and outlets to the third enclosed space 56 are positioned such that the second fluid 24 passes the tubes 44. This way, the third enclosed space 56 constitutes a second channel through which the second fluid 24 can flow.

Figure 3:
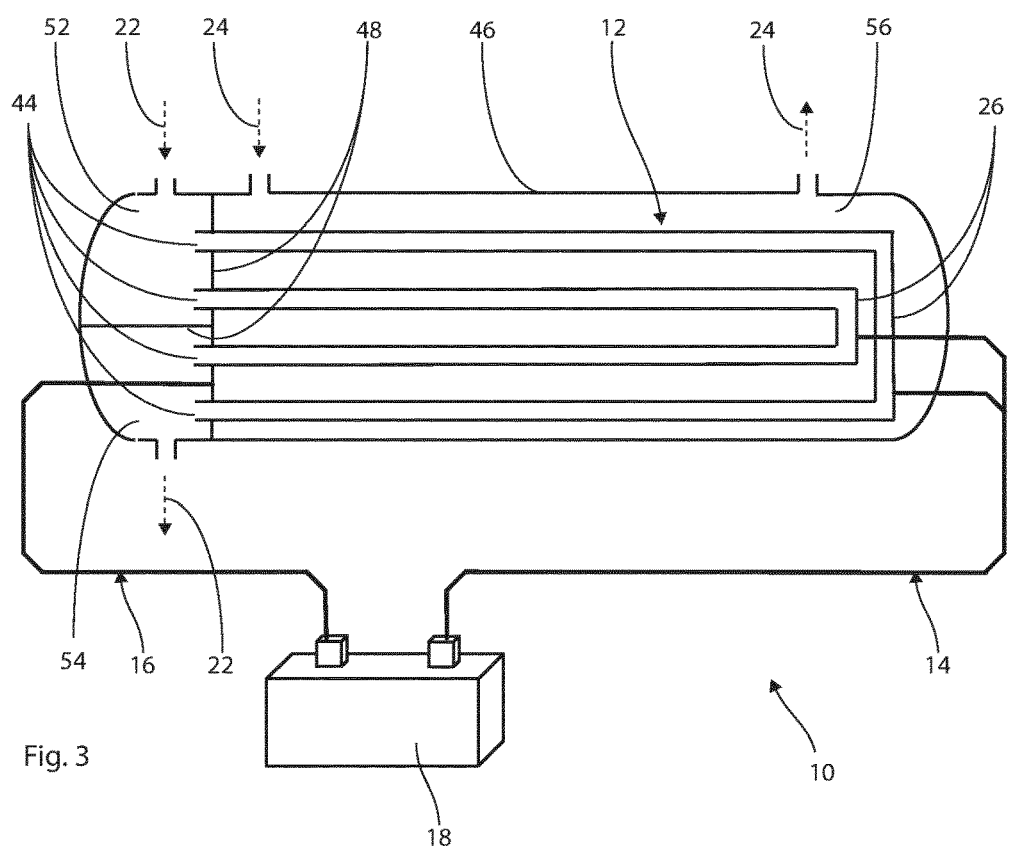
FIG. 3 is a schematic view of an embodiment of a heat exchanger assembly with a U-tube heat exchanger.
Figure 4:
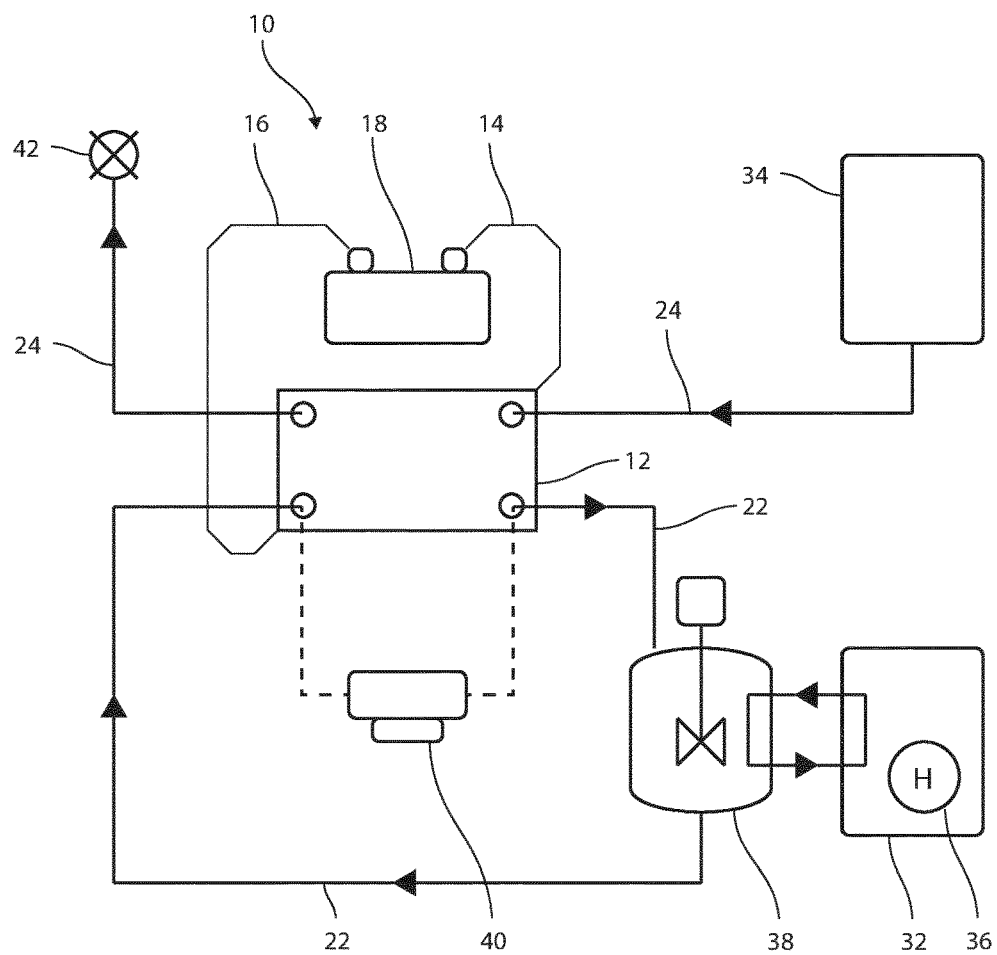
FIG. 4 is a schematic view of a test setup.
Figure 5:
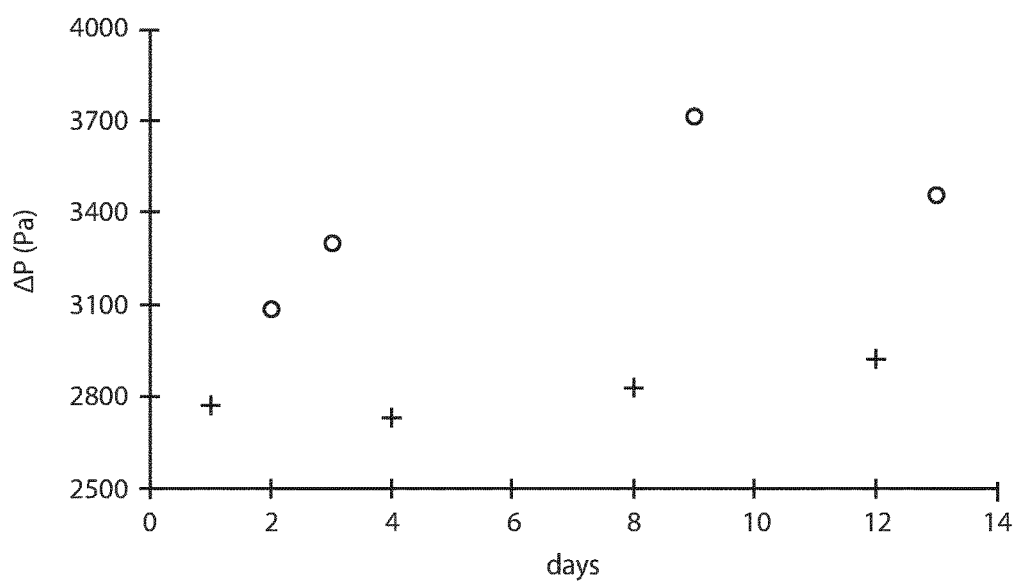
FIG. 5 is a graph showing the pressure drop (ΔP) over the heat exchanger in two different test runs.

Another embodiment of a heat exchanger assembly 10 is schematically illustrated in FIG. 3. Components having the same nature or function, or with similar nature or function, as in the embodiment described in relation to FIGS. 1 and 2 have been given the same reference number. The heat exchanger 12 is a shell and tube heat exchanger. It has a tube bundle of tubes 44 that are bent in a U-shape as shown in FIG. 2. The tubes 44 form the one or more partitions 26.

The embodiment shown in FIG. 3 differs from the embodiment shown in FIG. 2 in that it has no second tube plate 50. Instead, the tubes 44 are supported only by the first tube plate 48. The second enclosed space 54 is formed by the first tube plate 48 and the shell 46, and the third enclosed space 56 is formed by the first tube plate 48 and the shell 46, as is shown in FIG. 3. The first enclosed space 52 and the second enclosed space 54 are separated by an extension of the first tube plate 48. Each tube 44 extends from the first enclosed space 52 into the third enclosed space 56, bends and returns to the second enclosed space 54 that is juxtaposed to the first enclosed space 52. The first electrical connector 14 is composed of the first tube plate 48 and of an electric cable connecting the first tube plate 48 to the electrical power source 18. The second electrical connector 16 is composed of electric cables connecting the electrical power source 18 to each of the tubes 44 on the other end of the tube bundle.

EXAMPLE

A test setup used in a proof-of-concept is illustrated in FIG. 2. The setup included a heat exchanger assembly 10 as described in relation to FIG. 1. The electric conductivity of the stainless steel plates 20 of the heat exchanger 12 is high. Therefore, a 51 kOhm resistor (not shown) was placed in series with the heat exchanger 12 to limit the current.

The test setup has a first tank 32 containing water and a heater 36 arranged to heat the water in the first tank 32. The setup further has a jacketed tank 38 containing brackish sea water that constitutes a first fluid 22. The jacketed tank 38 is coupled to the first tank 32 so that heat can be received therefrom. The test setup also has a second tank 34 containing colder tap water constituting a second fluid 24.

The test setup further has pressure gauge 40. The different components are connected as indicated in FIG. 2. The setup has a number of valves and pumps (not shown) that generates and controls the flows indicated by arrows in FIG. 2. The setup is coupled to a drain 42 such that the tap water in the second tank 34 can empty from the setup after passing the heat exchanger 12. The setup also has a number of thermometers (not shown) for measuring the temperature of the first fluid 22 and the second fluid 24 at the respective inlet of the heat exchanger 12.

The following temperatures were measured by the thermometers: the inlet temperature of the first fluid 22 (Th,in) and the inlet temperature of the second fluid 24 (Tc,in). The pressure drop (ΔP) of the first fluid 22 over the heat exchanger 12 was measured using the pressure gauge. The pressure drop (ΔP) of the first fluid 22 was used to characterize the performance of the heat exchanger 12.

Two tests were run on the same setup, one with electrification and one without electrification, i.e. with or without an electric current supplied to the heat exchanger 12 by the electrical power source 18. All other test parameters were the same. The setup was cleaned before each test run. The same first fluid 22 (sea water) was used in both test runs. Both tests were run for 18 days.

The input temperature (Th,in) of the first fluid 22 (hot sea water) was held approximately constant at 40 degrees C., and the input temperature (Tc,in) of the second fluid 24 (cold tap water) was held approximately constant at 10 degrees C. The electrical power source 18 was operated at a peak current of about 0.54 mA, a peak voltage of about 80 V, and a frequency of 5 Hz.

After each test run, the heat exchanger 12 was dismantled and biofilm samples were taken from the inner surfaces of the separating partitions 26 of the heat exchanger 12 facing the first fluid 22 (sea water). Sterile cotton swabs were used, and the same swabbing pattern was repeated. Approximately 2 cm² were swabbed each time.

For both test runs, four biofilm samples were taken at four different points on the inner surfaces of the separating partitions 26. Each sample was then turned into triplicates in order to avoid contamination. The samples were analysed using laser-based flow cytometry for cell counting and differentiation of dead and viable bacteria. The average bacterial count is presented in Table 1.

TABLE 1

Average bacterial count from samples

|  | Not electrified | Electrified |
|---|---|---|
| Total number bacteria | 3608 | 321 |
| Viable number bacteria | 2264 | 50 |

The electrification of the heat exchanger 12 clearly results in a drop in the count of bacteria, both in total number and in the number of viable bacteria. The total number of bacteria is reduced to about 9%. The effect is even greater for viable bacteria, for which the number of bacteria is reduced to less than 3%. It can be concluded that the electrification greatly reduces the bacterial growth on the partitions of the heat exchanger facing the first fluid 22 (sea water).

FIG. 3 is a graph showing the pressure drop (ΔP) of the first fluid 22 over the heat exchanger 12 as a function of time. Crosses indicate the results for the electrified setup run, and circles indicate the results for the non-electrified setup run. It can be seen in the graph of FIG. 3 that the pressure drop (ΔP) increases with time for the non-electrified test run, while it is more or less constant for the electrified test run. After 14 days, the pressure difference is about 25% higher without electric current. It is contemplated that this change is caused by the greater microbiological growth in the non-electrified test run than in the electrified test run, and that the growth restricts the flow of the first fluid 22 through the heat exchanger 12. This results in a reduced dynamic pressure after the heat exchanger, which in extension leads to a greater pressure drop (ΔP). It can be concluded that the supply of electric current to the heat exchanger 12 prevents a pressure drop (ΔP) over the heat exchanger that is likely caused by the growth of microorganisms.

ITEM LIST 10 heat exchanger assembly
12 heat exchanger
14 first electrical connector
16 second electrical connector
18 electrical power source
20 plates
22 first fluid
24 second fluid
26 separating partitions
28 side section
30 corner section
32 first tank
34 second tank
36 heater
38 jacketed tank
40 pressure gauge
42 drain
44 tubes
46 shell
48 first tube plate
50 second tube plate
52 first enclosed space
54 second enclosed space
56 third enclosed space

The invention claimed is:
1. A heat exchanger assembly, comprising:
a heat exchanger, comprising a plurality of partitions, each of the plurality of partitions configured to separate a first fluid and a second fluid, and through which heat is transferrable between the first fluid and the second fluid, wherein the plurality of partitions are electrically connected to one another and share the same electric potential;

a first electrical connector and a second electrical connector that are operationally connected to the plurality of partitions of the heat exchanger; and an electrical power source operationally connected to the first electrical connector and the second electrical connector and configured to supply an electric current to the plurality of partitions of the heat exchanger via the first electrical connector and the second electrical connector for reducing growth of microorganisms in the heat exchanger.

2. The heat exchanger assembly according to claim 1, wherein the heat exchanger is configured to handle a liquid food product.

3. The heat exchanger assembly according to claim 1, comprising at least two partitions of the plurality of partitions that are structurally connected to one another.

4. The heat exchanger assembly according to claim 3, wherein the at least two partitions form one or more first channels through which the first fluid can flow.

5. The heat exchanger assembly according to claim 4, wherein the heat exchanger is a shell and tube heat exchanger comprising a tube bundle with tubes constituting the at least two partitions forming the one or more first channels.

6. The heat exchanger assembly according to claim 4, wherein the plurality of partitions form one or more second channels through which the second fluid can flow, wherein the heat exchanger is a plate heat exchanger comprising a plurality of plates forming the plurality of partitions, and wherein the plurality of plates form the one or more second channels.

7. The heat exchanger assembly according to claim 6, wherein the conditions for microbial growth is greater in the first fluid than in the second fluid, and the first electrical connector is structurally connected to a pair of adjacent plates of the plurality of plates, wherein the pair of adjacent plates is configured to enclose the first fluid.

8. The heat exchanger assembly according to claim 6, wherein the first electrical connector and the second electrical connector are structurally connected to the heat exchanger on opposite sides of the heat exchanger.

9. A method for reducing microbiological growth in a heat exchanger of a heat exchanger assembly according to claim 1, wherein the method comprises:
(a) providing a flow of the first fluid and a flow of the second fluid in the heat exchanger; and
(b) supplying an electric current to the plurality of partitions of the heat exchanger with the electrical power source.

10. A pasteurizer for heat treatment of a liquid food product, wherein the pasteurizer comprises a heat exchanger assembly according to claim 1 for heating or cooling the liquid food product.

* * * * *